United States Patent
Thompson et al.

(10) Patent No.: US 9,982,345 B2
(45) Date of Patent: May 29, 2018

(54) DEPOSITION OF METAL FILMS USING BETA-HYDROGEN FREE PRECURSORS

(71) Applicant: Applied Materials, Inc., Santa Clara, CA (US)

(72) Inventors: David Thompson, San Jose, CA (US); David Knapp, Santa Clara, CA (US); Jeffrey W. Anthis, San Jose, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 0 days. days.

(21) Appl. No.: 15/210,352

(22) Filed: Jul. 14, 2016

(65) Prior Publication Data
US 2017/0016113 A1    Jan. 19, 2017

Related U.S. Application Data

(60) Provisional application No. 62/192,212, filed on Jul. 14, 2015.

(51) Int. Cl.
*C23C 16/18* (2006.01)
*C23C 16/455* (2006.01)
*C07F 5/06* (2006.01)

(52) U.S. Cl.
CPC ........ *C23C 16/45536* (2013.01); *C07F 5/062* (2013.01); *C23C 16/18* (2013.01); *C23C 16/45553* (2013.01)

(58) Field of Classification Search
CPC ........ C23C 16/20; C23C 16/18; C23C 16/403
See application file for complete search history.

(56) References Cited

U.S. PATENT DOCUMENTS

| | | | |
|---|---|---|---|
| 4,960,916 A * | 10/1990 | Pazik | C07F 9/904 556/70 |
| 5,621,130 A * | 4/1997 | Ando | G03G 5/0578 204/157.64 |
| 5,863,836 A * | 1/1999 | Jones | C23C 16/18 438/681 |
| 6,077,571 A * | 6/2000 | Kaloyeros | C23C 14/16 257/E21.17 |
| 7,691,664 B2 | 4/2010 | Kodas et al. | |
| 2003/0124259 A1 | 7/2003 | Kodas et al. | |
| 2004/0198025 A1 * | 10/2004 | Derderian | C23C 16/06 438/476 |
| 2006/0035462 A1 | 2/2006 | Millward | |
| 2007/0237698 A1 * | 10/2007 | Clark | C23C 16/34 423/263 |
| 2008/0085962 A1 | 4/2008 | Simone et al. | |
| 2009/0209777 A1 * | 8/2009 | Thompson | C07F 15/0053 556/136 |
| 2011/0262660 A1 * | 10/2011 | Ishii | C23C 16/305 427/569 |
| 2013/0064970 A1 | 3/2013 | Goh et al. | |
| 2013/0217840 A1 | 8/2013 | McCleskey et al. | |
| 2016/0118261 A1 * | 4/2016 | Haukka | H01L 29/4966 438/592 |

* cited by examiner

*Primary Examiner* — David P Turocy
(74) *Attorney, Agent, or Firm* — Servilla Whitney LLC

(57) ABSTRACT

Methods of depositing a metal-containing film by exposing a substrate surface to a first precursor and a reactant, where one or more of the first precursor and the react comprises a compound having the general formula of one or more of $M(XR_3)_2$, $M(XR_3)_3$, $M(XR_3)_4$, $M(XR_3)_5$ and $M(XR_3)_6$, where M is selected from the group consisting of Al, Ti, Ta, Zr, La, Hf, Ce, Zn, Cr, Sn, V and combinations thereof, each X is one or more of C, Si and Ge and each R is independently a methyl or ethyl group and comprises substantially no β-H.

18 Claims, No Drawings

DEPOSITION OF METAL FILMS USING BETA-HYDROGEN FREE PRECURSORS

CROSS-REFERENCE TO RELATED APPLICATIONS

This application claims priority to U.S. Provisional Application No. 62/192,212, filed Jul. 14, 2015, the entire disclosure of which is hereby incorporated by reference herein.

TECHNICAL FIELD

Embodiments of the present disclosure generally relate to film deposition, and specifically to the deposition of films using metal precursors that a substantially free of β-Hydrogen.

BACKGROUND

Deposition of thin films on a substrate surface is an important process in a variety of industries including semiconductor processing, diffusion barrier coatings and dielectrics for magnetic read/write heads. In the semiconductor industry, in particular, miniaturization requires atomic level control of thin film deposition to produce conformal coatings on high aspect structures.

One method for deposition of thin films is atomic layer deposition (ALD). Most ALD processes are based on binary reaction sequences, where each of the two surface reactions occurs sequentially. Because the surface reactions are sequential, the two gas phase reactants are not in contact, and possible gas phase reactions that may form and deposit particles are limited. While ALD tends to result in more conformal films than traditional chemical vapor deposition (CVD), prior art processes for ALD have been most effective for deposition of metal oxide and metal nitride films. Although a few processes have been developed that are effective for deposition of elemental ruthenium and other late transition metals, in general ALD processes for deposition of pure metal have not been sufficiently successful to be adopted commercially.

Pure metal films of aluminum have many applications in the integrated circuit manufacturing process. Aluminum precursors tend to decompose or isomerize inside the ampoules used as reactive gas sources, leading to process drift. Therefore, there is a need in the art for classes of compounds that are less likely to decompose or isomerize in the ampoules, and are reactive for CVD and ALD processes.

SUMMARY

One or more embodiments of the disclosure are directed to methods of depositing a film. At least a portion of a substrate surface is exposed to a first precursor comprising a compound having the general structure

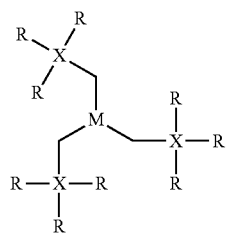

where M is a metal, each X is independently C, Si or Ge and each R comprises substantially no H. At least a portion of the substrate surface is exposed to a reactant to deposit a metal-containing film on the substrate surface.

Additional embodiments of the disclosure are directed to methods of depositing a film. At least a portion of a substrate surface is exposed to a first precursor and a reactant. One or more of the first precursor and the reactant comprises a compound having the general structure

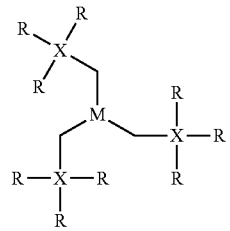

where M is Al, each X is independently C, Si and Ge, and each R is independently an alkyl group and comprises substantially no β-H.

Further embodiments of the disclosure are directed to methods of depositing a film. At least a portion of a substrate surface is exposed to a first precursor. At least a portion of the substrate surface is exposed to a reactant comprising a compound having the general formula of one or more of $M(XR_3)_2$, $M(XR_3)_3$, $M(XR_3)_4$, $M(XR_3)_5$ and $M(XR_3)_6$, where M is selected from the group consisting of Al, Ti, Ta, Zr, La, Hf, Ce, Zn, Cr, Sn, V and combinations thereof, each X is one or more of C, Si and Ge and each R is independently a methyl or ethyl group and comprises substantially no β-H.

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

Embodiments of the disclosure are directed to the use of aluminum precursors that do not have β-Hydrogen groups for the deposition of Al-containing films as well as films that use aluminum precursors as a reductant. β-Hydride elimination is a decomposition mechanism in organometallic chemistry and can lead to low thermal stability and potential isomerization of the precursors. (Crabree, R. H. *The Organometallic Chemistry of the Transition Metals, Second Edition*, John Wiley & Sons 1994.) Scheme (I) is an example of β-Hydride elimination from triethylaluminum.

Embodiments of the disclosure are directed to compounds and uses of the compounds that are less likely to decompose or isomerize inside the ampoule leading to process drift. Embodiments of the disclosure are directed to compounds, and uses, that will allow depositions requiring Al precursors to run at higher temperature.

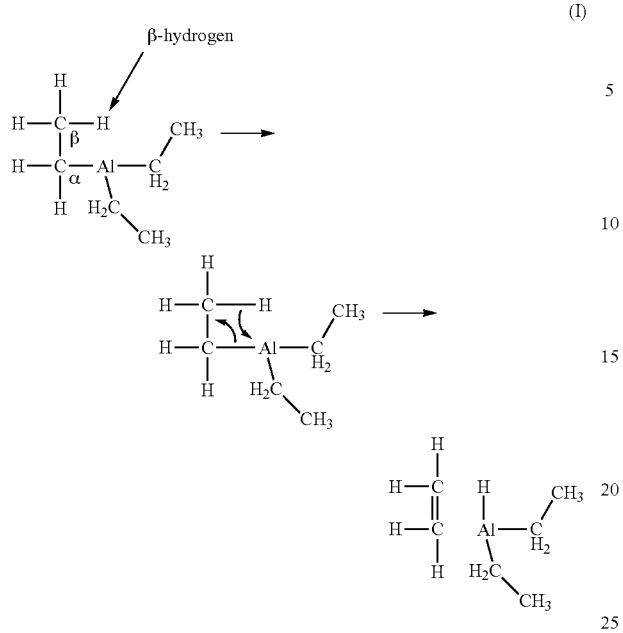

(I)

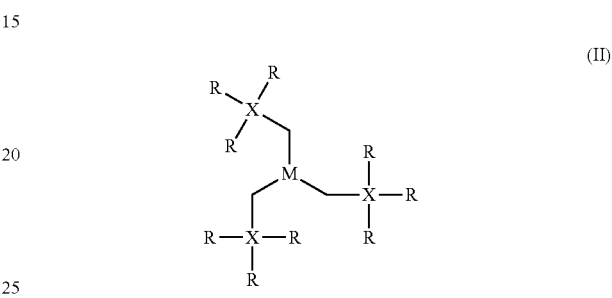

(II)

As used in this specification and the appended claims, the term "substrate" and "wafer" are used interchangeably, both referring to a surface, or portion of a surface, upon which a process acts. Those skilled in the art will understand that reference to a substrate can also refer to only a portion of the substrate, unless the context clearly indicates otherwise. Additionally, reference to depositing on a substrate can mean both a bare substrate and a substrate with one or more films or features deposited or formed thereon.

As used in this specification and the appended claims, the terms "reactive gas", "precursor", "reactant", and the like, are used interchangeably to mean a gas that includes a species which is reactive in an atomic layer deposition process. For example, a first "reactive gas" may simply adsorb onto the surface of a substrate and be available for further chemical reaction with a second reactive gas.

A "substrate" as used herein, refers to any substrate or material surface formed on a substrate upon which film processing is performed during a fabrication process. In some embodiments, the substrate is a rigid, discrete, generally planar substrate. As used in this specification and the appended claims, the term "discrete" when referring to a substrate means that the substrate has a fixed dimension. The substrate of one or more embodiments is a semiconductor substrate, such as a 200 mm or 300 mm diameter silicon substrate. For example, a substrate surface on which processing can be performed include materials such as silicon, silicon oxide, strained silicon, silicon on insulator (SOI), carbon doped silicon oxides, silicon nitride, doped silicon, germanium, gallium arsenide, glass, sapphire, and any other materials such as metals, metal nitrides, metal alloys, and other conductive materials, depending on the application. Substrates include, without limitation, semiconductor wafers. Substrates may be exposed to a pretreatment process to polish, etch, reduce, oxidize, hydroxylate, anneal and/or bake the substrate surface. In addition to film processing directly on the surface of the substrate itself, in the present disclosure any of the film processing steps disclosed may also be performed on an underlayer formed on the substrate as disclosed in more detail below, and the term "substrate surface" is intended to include such underlayer as the context indicates.

As used herein "pure metal film" refers to a film that comprises substantially only one metal. The term "substantially only one metal" means that there is greater than about 95% of the subject metal on an atomic basis. As used herein "pure metal alloy" refers to a film that comprises two or more different metal species and less than about 5% other elements on an atomic basis. For example, a pure Al—Ti alloy film comprises at least about 95% Al and Ti (sum) and may have up to about 5% carbon on an atomic basis.

One or more embodiments of the disclosure are directed to processes that use alkyl metal precursors that do not have β-H fragments to increase thermal stability and reduce the potential for isomerization in the ampoule. Structure (II) is a general structure for a precursor with no β-H where M is a metal, X is C, Si or Ge, and each R is independently an alkyl or comprises substantially no β-H. Each of the X groups can be independently selected from C, Si or Ge. Each of the R groups in structure (II) can have structural identities independent from any other R group so that there can in the range of 1 to 9 different R groups.

In some embodiments, the compound having the structure (II) can be used as a metal precursor in a process that deposits the metal onto the substrate surface. In one or more embodiments, the compound having the structure (II) can be used as a reactant and the deposited film comprises substantially no metal from the reactant. For example, if the metal of structure (II) is aluminum, the final film might comprise substantially no aluminum. As used in this specification and the appended claims, the term "substantially no" used in this regard means that there is less than about 5% on an atomic basis.

Some non-limiting examples of suitable compounds according to structure (II) include

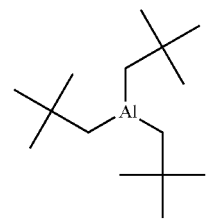

tris(neopentylidine)aluminum

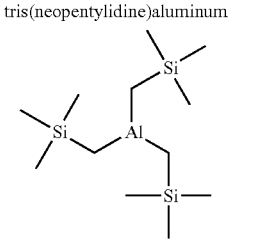

tris(trimethylsilylmethylene)aluminum

One or more embodiments of the disclosure are directed to methods of depositing a film. The method comprises exposing at least a portion of a substrate surface to a first precursor comprising a compound having the general structure (II). At least a portion of the substrate surface is exposed to a reactant to deposit a metal-containing film on the substrate surface. Metal-containing films can be, for example, pure metal films, metal alloy films, metal oxides, metal nitrides or metal oxynitrides. The type of metal-containing film formed depends on, for example, the species used as the precursor or the reactant.

The metal can be any suitable metal M. Suitable metals include, but are not limited to Al, Ti, Ta, Zr, La, Hf, Ce, Zn, Cr, Sn, V and/or combinations thereof. In some embodiments, the metal in the compound having the structure (II) comprises aluminum. The structure (II) may also be referred to as having the general formula $M(XR_3)_3$. In some embodiments, depending on the metal coordination, the compound may have a general formula of $M(XR_3)_2$ or $M(XR_3)_4$ or $M(XR_3)_5$ or $M(XR_3)_6$, where M is a metal, X is C, Si or Ge, and each R is independently an alkyl or comprises substantially no β-H.

Each of the X groups in the compound having the structure (II) can be independently C, Si or Ge. In some embodiments, each of the X atoms is C. In some embodiments, each of the X atoms is Si. In some embodiments, each of the X atoms is Ge. In some embodiments, the X atoms are a mixture of two or more of C, Si and Ge.

In some embodiments, each R is independently an alkyl. This means that each R group is an alkyl group but each of the R groups does not need to be the same alkyl group. In some embodiments, each of the R groups are substantially the same species. As used in this specification and the appended claims, the term "substantially the same" used in this regard means that greater than about 95% of the R groups are the same. In some embodiments, each of the R groups is one of methyl and ethyl.

Some embodiments of the disclosure are directed to methods of depositing a film comprising exposing at least a portion of a substrate surface to a first precursor and a reactant. One or more of the first precursor and the reactant comprises a compound having the general structure

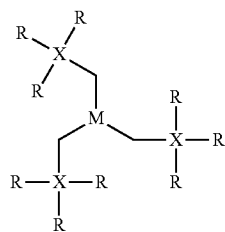

where M is Al, each X is independently C, Si and Ge, and each R is independently an alkyl group and comprises substantially no β-H.

In some embodiments, the first precursor comprises the compound with the general structure (II) and the film comprises substantially pure aluminum, or a substantially pure aluminum alloy.

In some embodiments, the reactant comprises the compound with the general structure (II) and the film comprises substantially no aluminum, or a substantially pure aluminum alloy.

Some embodiments of the disclosure further comprise exposing the substrate surface to a second precursor. The second precursor can be exposed to the substrate at the same time as the first precursor and/or the reactant, or at a separate time from either or both. For example, the first precursor may have the structure (II) and the second precursor may have the same structure (II) with a different metal than the first precursor. Mixed metal films can be formed by using different first and second precursors.

In some embodiments, exposing the substrate surface to the first precursor and the reactant occurs sequentially. For example, an ALD type process so that the substrate surface (or portion thereof) is exposed to the first precursor and the reactant sequentially or substantially sequentially. In some embodiments, exposing the substrate surface to the first precursor and the reactant occurs simultaneously. For example, a CVD type process in which both the first precursor and the reactant are flowed into the processing chamber at the same time, allowing gas phase reactions of the first precursor and the reactant.

In some embodiments, one or more layers may be formed during a plasma enhanced atomic layer deposition (PEALD) process. In some processes, the use of plasma provides sufficient energy to promote a species into the excited state where surface reactions become favorable and likely. Introducing the plasma into the process can be continuous or pulsed. In some embodiments, sequential pulses of precursors (or reactive gases) and plasma are used to process a layer. In some embodiments, the reagents may be ionized either locally (i.e., within the processing area) or remotely (i.e., outside the processing area). In some embodiments, remote ionization can occur upstream of the deposition chamber such that ions or other energetic or light emitting species are not in direct contact with the depositing film. In some PEALD processes, the plasma is generated external from the processing chamber, such as by a remote plasma generator system. The plasma may be generated via any suitable plasma generation process or technique known to those skilled in the art. For example, plasma may be generated by one or more of a microwave (MW) frequency generator or a radio frequency (RF) generator. The frequency of the plasma may be tuned depending on the specific reactive species being used. Suitable frequencies include, but are not limited to, 2 MHz, 13.56 MHz, 40 MHz, 60 MHz and 100 MHz, as well as in the GHz range, such as 2.45 GHz for the most common microwave generator. Although plasmas may be used during the deposition processes disclosed herein, plasmas may not be used. Indeed, other embodiments relate to deposition processes under very mild conditions without a plasma.

According to one or more embodiments, the substrate is subjected to processing prior to and/or after forming the layer. This processing can be performed in the same chamber or in one or more separate processing chambers. In some embodiments, the substrate is moved from the first chamber to a separate, second chamber for further processing. The substrate can be moved directly from the first chamber to the separate processing chamber, or the substrate can be moved from the first chamber to one or more transfer chambers, and then moved to the separate processing chamber. Accordingly, the processing apparatus may comprise multiple chambers in communication with a transfer station. An apparatus of this sort may be referred to as a "cluster tool" or "clustered system", and the like.

Generally, a cluster tool is a modular system comprising multiple chambers which perform various functions including substrate center-finding and orientation, degassing, annealing, deposition and/or etching. According to one or more embodiments, a cluster tool includes at least a first chamber and a central transfer chamber. The central transfer chamber may house a robot that can shuttle substrates between and among processing chambers and load lock chambers. The transfer chamber is typically maintained at a vacuum condition and provides an intermediate stage for shuttling substrates from one chamber to another and/or to a load lock chamber positioned at a front end of the cluster tool. Two well-known cluster tools which may be adapted for the present disclosure are the Centura® and the Endura®, both available from Applied Materials, Inc., of Santa Clara, Calif. However, the exact arrangement and combination of chambers may be altered for purposes of performing specific portions of a process as described herein. Other processing chambers which may be used include, but are not limited to, cyclical layer deposition (CLD), atomic layer deposition (ALD), chemical vapor deposition (CVD), physical vapor deposition (PVD), etch, pre-clean, chemical clean, thermal treatment such as RTP, plasma nitridation, degas, orientation, hydroxylation and other substrate processes. By carrying out processes in a chamber on a cluster tool, surface contamination of the substrate with atmospheric impurities can be avoided without oxidation prior to depositing a subsequent film.

According to one or more embodiments, the substrate is continuously under vacuum or "load lock" conditions, and is not exposed to ambient air when being moved from one chamber to the next. The transfer chambers are thus under vacuum and are "pumped down" under vacuum pressure. Inert gases may be present in the processing chambers or the transfer chambers. In some embodiments, an inert gas is used as a purge gas to remove some or all of the reactants after forming the layer on the surface of the substrate. According to one or more embodiments, a purge gas is injected at the exit of the deposition chamber to prevent reactants from moving from the deposition chamber to the transfer chamber and/or additional processing chamber. Thus, the flow of inert gas forms a curtain at the exit of the chamber.

During processing, the substrate can be heated or cooled. Such heating or cooling can be accomplished by any suitable means including, but not limited to, changing the temperature of the substrate support (e.g., susceptor) and flowing heated or cooled gases to the substrate surface. In some embodiments, the substrate support includes a heater/cooler which can be controlled to change the substrate temperature conductively. In one or more embodiments, the gases (either reactive gases or inert gases) being employed are heated or cooled to locally change the substrate temperature. In some embodiments, a heater/cooler is positioned within the chamber adjacent the substrate surface to convectively change the substrate temperature.

The substrate can also be stationary or rotated during processing. A rotating substrate can be rotated continuously or in discreet steps. For example, a substrate may be rotated throughout the entire process, or the substrate can be rotated by a small amount between exposure to different reactive or purge gases. Rotating the substrate during processing (either continuously or in steps) may help produce a more uniform deposition or etch by minimizing the effect of, for example, local variability in gas flow geometries.

Reference throughout this specification to "one embodiment," "some embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in some embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A method of depositing a film, the method comprising:
   exposing at least a portion of a substrate surface to a first precursor comprising a compound having the general structure

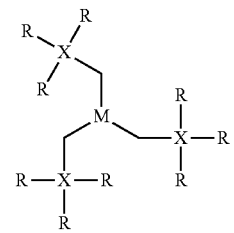

where M is a metal, each X is independently C, Si or Ge with the proviso that at least one X is Ge and each R is not H; and
   exposing at least a portion of the substrate surface to a reactant to deposit a metal-containing film on the substrate surface.

2. The method of claim 1, wherein M is Al.

3. The method of claim 1, wherein at least one X is Si.

4. The method of claim 1, wherein each R is independently an alkyl.

5. The method of claim 1, wherein exposing the substrate surface to the first precursor and the reactant occurs sequentially.

6. The method of claim 1, wherein exposing the substrate surface to the first precursor and the reactant occurs simultaneously.

7. The method of claim 1, wherein the reactant comprises a metal halide.

8. The method of claim 1, wherein the metal-containing film consists essentially of a substantially pure metal.

9. The method of claim 1, wherein the metal-containing film consists essentially of a substantially pure metal alloy.

10. The method of claim 1, wherein the metal-containing film comprises a metal nitride.

11. The method of claim 1, wherein the metal-containing film comprises a metal oxide.

12. A method of depositing a film, the method comprising exposing at least a portion of a substrate surface to a first precursor and a reactant, one or more of the first precursor and the reactant comprising a compound having the general structure

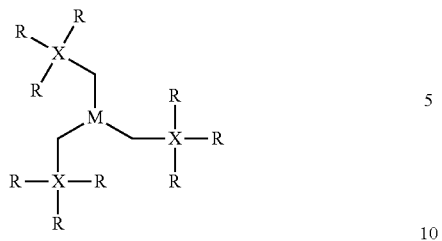

where M is Al, each X is independently C, Si or Ge with the proviso that at least one X is Ge, each R is independently an alkyl group, and the compound comprises substantially no β-H.

13. The method of claim 12, wherein the film consists essentially of substantially pure aluminum.

14. The method of claim 12, wherein the film consists essentially of substantially pure aluminum alloy.

15. The method of claim 12, wherein the reactant comprises the compound with the general structure and the film comprises substantially no aluminum.

16. The method of claim 12, wherein the first precursor and the reactant are sequentially exposed to the substrate surface.

17. The method of claim 12, wherein the first precursor and the reactant are exposed to the substrate surface at the same time.

18. The method of claim 12, further comprising exposing the substrate surface to a second precursor during, before or after exposure to the first precursor and/or reactant.

* * * * *